United States Patent [19]

Aday et al.

[11] Patent Number: 4,533,041

[45] Date of Patent: Aug. 6, 1985

[54] MULTISTRAND SUTURE PACKAGE WITH SINGLE STRAND SUTURE DISPENSING

[75] Inventors: Jorge L. Aday, Lambertville; Robert J. Cerwin, Pittstown, both of N.J.

[73] Assignee: Ethicon, Inc., Somerville, N.J.

[21] Appl. No.: 636,424

[22] Filed: Jul. 31, 1984

[51] Int. Cl.³ ............................................. A61L 17/02
[52] U.S. Cl. .................................. 206/63.3; 206/388
[58] Field of Search ...................... 206/63.3, 388, 227, 206/380

[56] References Cited

U.S. PATENT DOCUMENTS

| | | | |
|---|---|---|---|
| 3,985,227 | 10/1976 | Thyen et al. | 206/63.3 |
| 4,034,850 | 7/1977 | Mandel et al. | 206/63.3 |
| 4,135,623 | 1/1979 | Thyen | 206/63.3 |

*Primary Examiner*—Joseph Man-Fu Moy
*Attorney, Agent, or Firm*—Robert L. Minier

[57] ABSTRACT

A folder and retainer for a plurality of sutures. The folder and retainer comprises a plurality of panels forming a compartment between adjacent panels with a single loop of sutures disposed in any single compartment to provide for removal of an individual suture from the folder and retainer without entanglement of the sutures.

14 Claims, 10 Drawing Figures

FIG-3
FIG-4
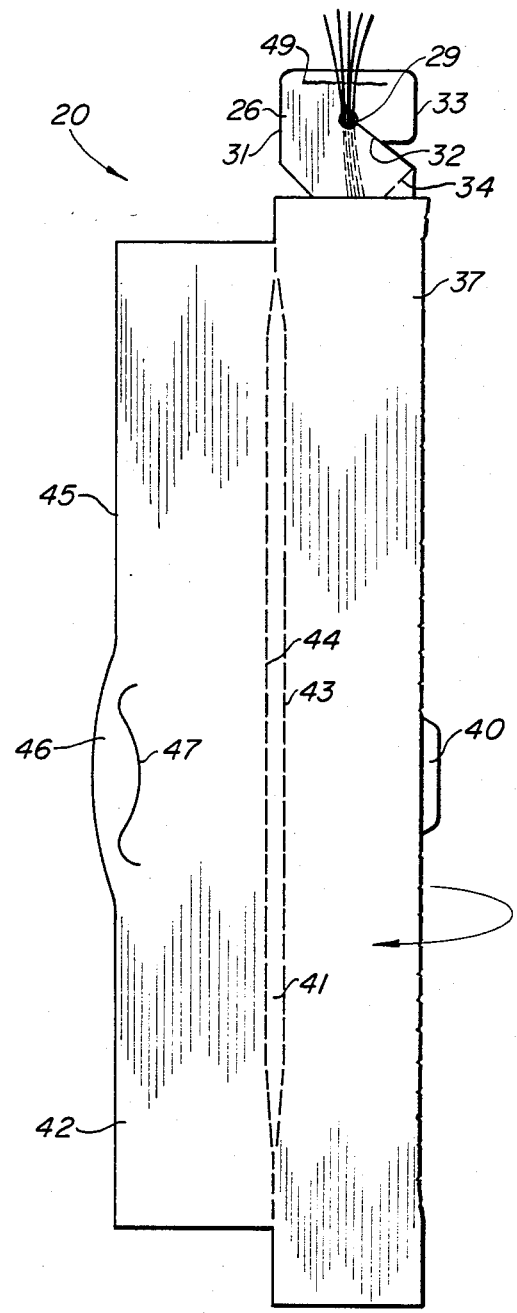
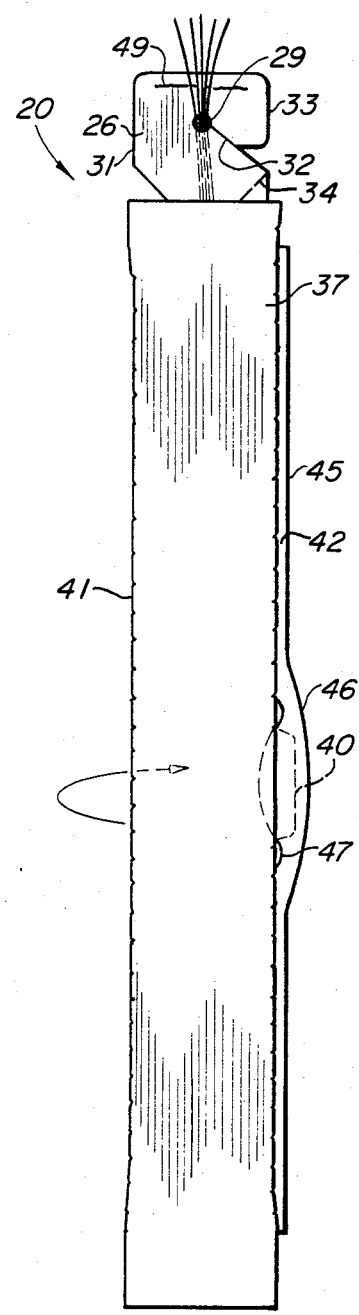

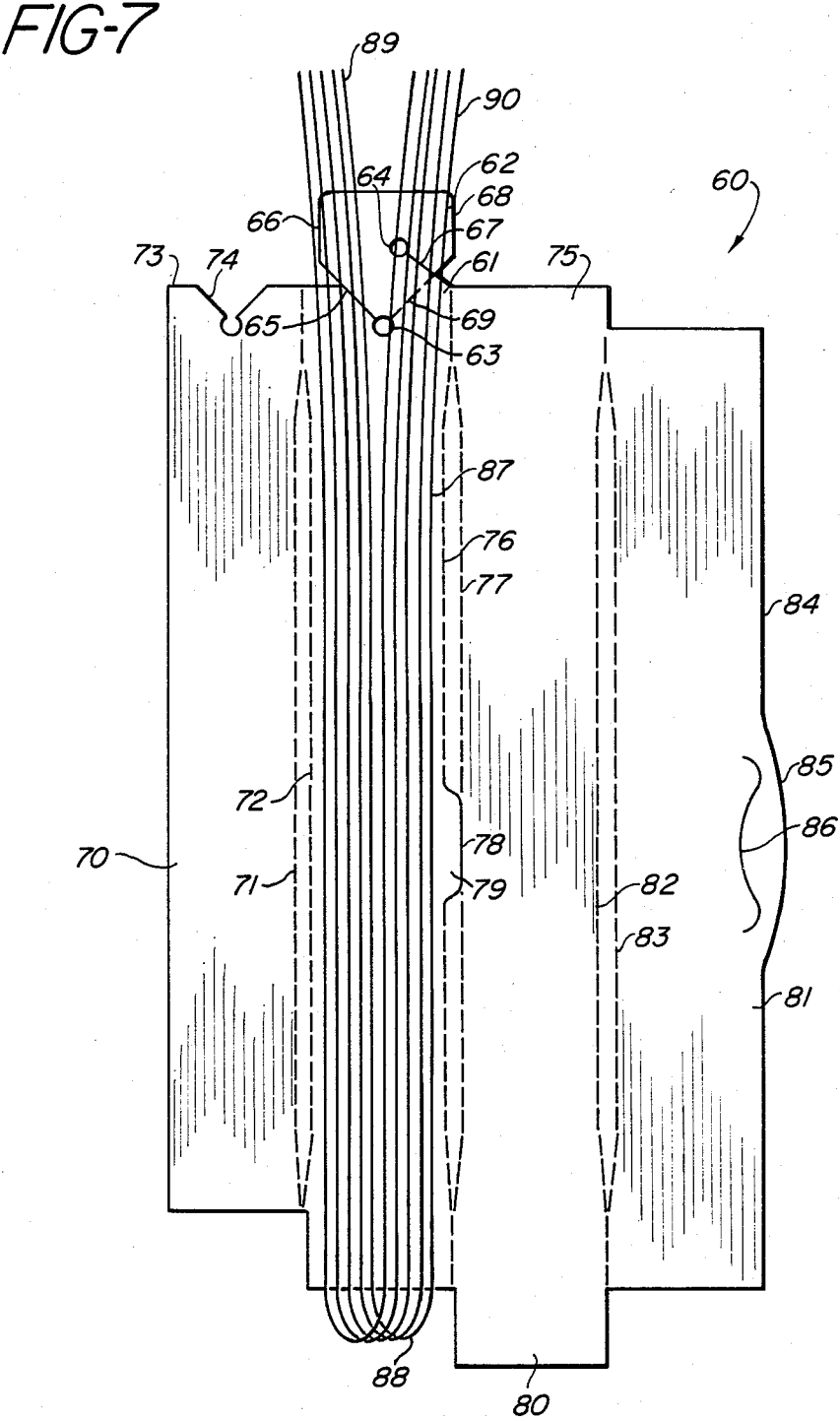

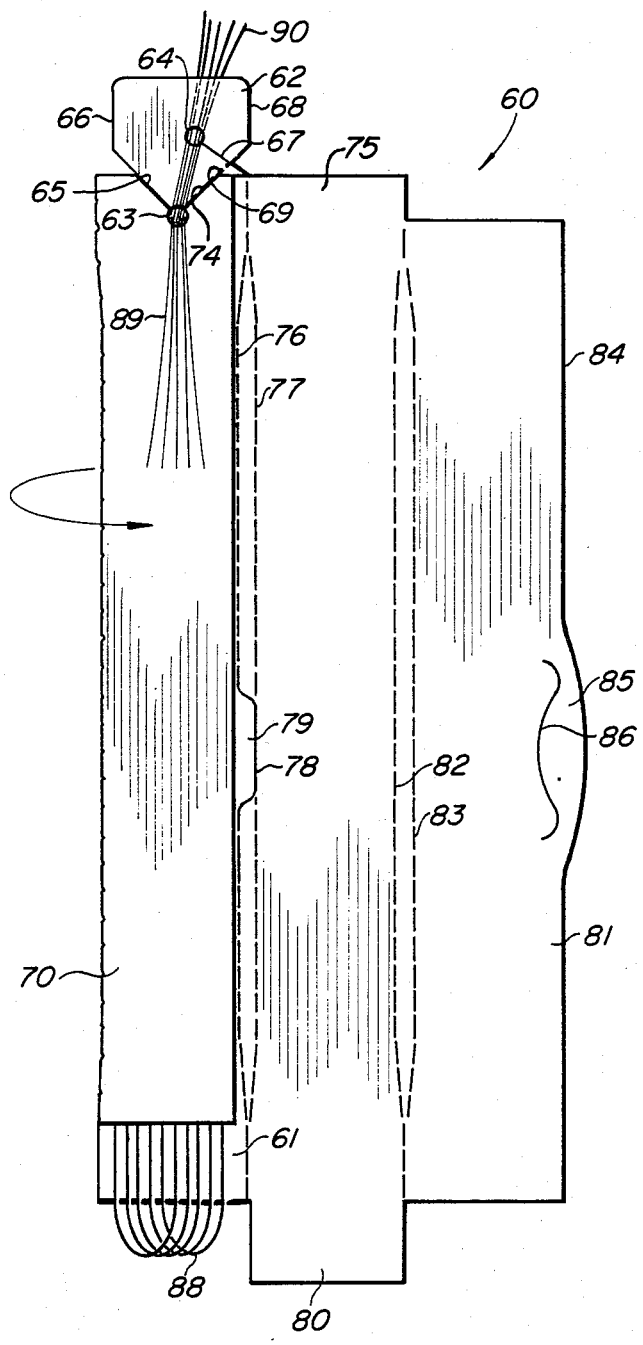

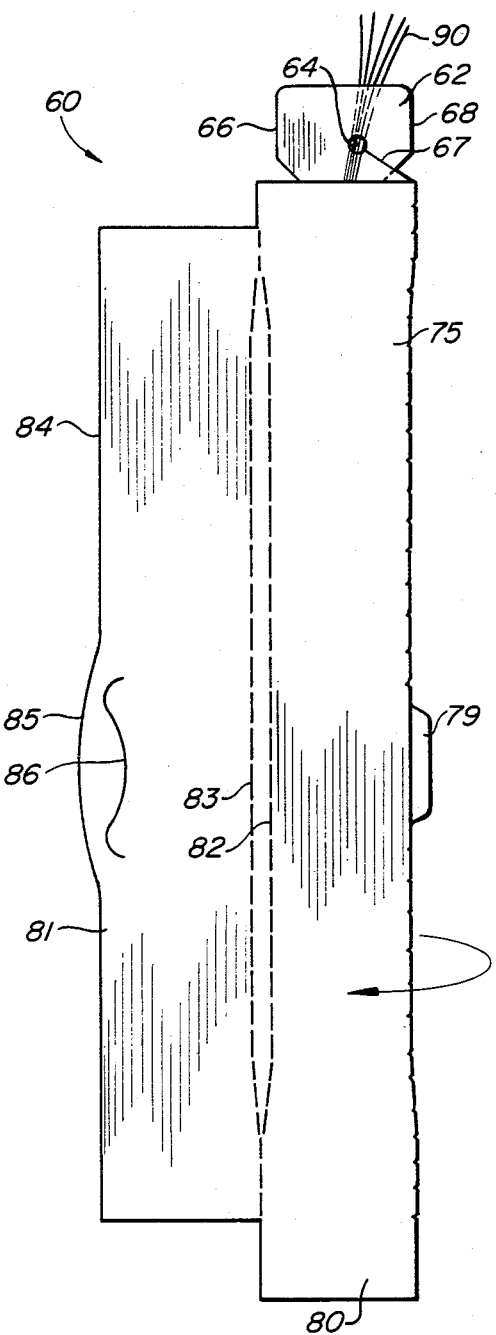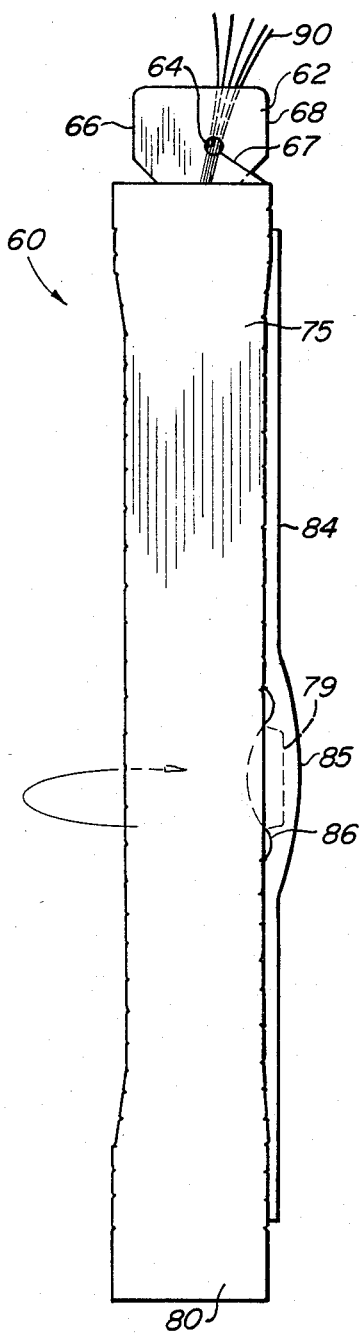

MULTISTRAND SUTURE PACKAGE WITH SINGLE STRAND SUTURE DISPENSING

BACKGROUND OF THE INVENTION

The present invention relates to packages for surgical sutures and more particularly to a multiple panel folded retainer for a plurality of sutures which retainer allows for the single strand dispensing of the sutures.

Packages for surgical sutures are constructed according to the nature of the suture and its intended use. Also, the packages are designed taking into consideration the economics of the package and the method of placing the sutures in the package. In general, the ideal package protects the suture during handling and storage yet allows the suture to be removed with a minimum of difficult, and the package itself is economical to produce.

The more popular suture packages consist of a folded paper or cardboard retainer with the sutures therein and with the retainer contained in a sterile hermitically sealed envelope. In many instances the sterility of the suture and envelope are maintained by a second sealed outer wrap. When the suture is to be used, the outer wrap is opened in the operating room and the sealed envelope deposited in a sterile area. Sterile personnel thereupon tear open the sterile envelope providing access to the suture.

Many packages have been developed which contain a plurality of sutures and have been designed in such a way as to allow all the sutures to be removed from the package or to allow a single suture to be removed from the package. The packages must be designed so that a single suture can be removed from the package of multiple sutures without disrupting or entangling and rendering virtually useless the remaining sutures in the package. A number of ways have been developed to allow for single strand dispensing from a multiple suture package. In certain instances the package has been designed with a channel in the package and with the sutures laid in that channel so that as one suture is removed from the channel, the other sutures will remain in place in the channel. An example of such a package is shown in U.S. Pat. No. 4,424,898. Another technique for designing such a package is to design the package so it has individual and adjacent compartments with each compartment containing a suture. U.S. Pat. No. 3,759,376 discloses such a package. Another technique for producing such a package is to place some frictional material on the surface of the package which is to engage the sutures. Such frictional material will hold the sutures in place, yet will allow a single suture to be removed from the package. An example of such a package is shown in copending U.S. patent application Ser. No. 532,632 filed Sept. 15, 1983.

Yet another technique for producing a multistrand package allowing for single strand dispensing is to wind the sutures in a very specific manner so that they lay in the package in a manner that will allow single strand delivery from the wind. An example of such a technique for winding sutures in such a suture package is disclosed in U.S. Pat. No. 4,089,409. Still other multistrand suture packages are disclosed in U.S. Pat. Nos. 4,126,221 and 4,253,563.

In producing a multistrand suture package, a number of things are important. Perhaps of primary importance is that the suture package should hold all the sutures while allowing dispensing of individual sutures without disrupting or dislodging or entangling the remaining sutures in the package. Also, perhaps of equal importance is that the single suture should be easily removed from the package with a minimum of force. Of course, in all suture packages economics and cost are of importance as well as is the simplicity of the package to keep the expense in packaging sutures in the package to a minimum.

It is an object of the present invention to produce a multistrand suture package which allows for single strand deliver of sutures from that package with little or no disruption of the remaining sutures in the package. It is another object of the present invention to produce a package where a single strand suture may be removed from the package with a minimum of force. It is still another object of the present invention to produce a package which is economical to produce. It is yet a further object of the present invention to produce a multistrand suture package which is easily filled with sutures in a simple and economical manner.

These and other objects of the present invention will become more apparent upon the reading of the ensuing description and claims.

SUMMARY OF THE INVENTION

The present invention provides an elongated rectangular suture folder and retainer for a plurality of sutures. The retainer allows for either single strand dispensing of the sutures of if desired, multiple strand dispensing of the sutures. The folder and retainer comprise a first suture winding panel having an elongated rectangular shape. Foldably connected to this first suture winding panel is a second suture holding panel. The second panel also has an elongated rectangular shape and is foldably connected to the first panel along one of the longer longitudinal edges of the first panel. Either the first or second panel has an extension extending beyond the shorter edge of said other panel so that there is at least a portion of this extension that extends beyond the edge of both the first and second panels. The folder and retainer include a first opening disposed in the panel having the extension with the opening disposed substantially adjacent the extension.

A second opening is disposed in the extension of the panel. These openings are preferably aligned longitudinally though they may be offset slightly—that is, one of the openings may be offset with respect to the other opening by an angle of 45° or less. The angle is measured from the longitudinal line extending through the panel. The folder and retainer include a first slit extending from an edge of the extension and connected to the first opening. The folder and retainer also include a second slit extending from an edge of the extension to the second opening. In the preferred emodiments of the folder and retainer of the present invention the extension is removable from the folder and retainer so that the extension and all the sutures connected thereto maybe removed from the folder and retainer in one operation. One technique for providing for a removable extension is to place a perforated line extending from the edge of the extension opposite to the edge containing the first slit to the first opening which perforated line may be torn so that the extension may be removed along with all the sutures from the folder and retainer. In these preferred embodiments the size and type of suture is indicated on the extension so that when the sutures and extension are removed from the folder and retainer, the user can know exactly what sutures are available. In the folder and retainer of the present invention, a third cover panel is foldably connected to the other or free longitudinal edge of the first suture winding panel. This third covering panel actually will cover portions of the sutures which are disposed on top of the second suture holding panel. The folder and retainer include a fourth locking panel foldably connected to the other or free longitudinal edge of the third covering panel. In certain embodiments of the present invention, there is a slit placed in the foldable line between the first suture winding panel and the third suture cover panel. Along with this slit there is an appropriate tab placed along the free longitudinal edge of the fourth locking panel. When the panel is folded with the second suture holding panel folded on top of the first suture winding panel and the third cover panel folded on top of the second suture holding panel, the fourth locking panel may then be folded behind the first suture winding panel and the tab and slit engaged to lock the folded panel in its folded configuration. In the preferred embodiments of the present invention, the folds between panels are actually double fold lines to form a gusset between the first and second panel, the second and third panel, and the third and fourth panel. These gussets give some depth to the folded retainer so that if the retainer is held with slight pressure as a suture is being removed, that pressure is not transmitted to the sutures themselves which would retard or restrict the dispensing of the sutures from the panel. In other embodiments of the present invention, one of the panels, preferably the third cover panel, will extend beyond the end of the other suture panels. This extension allows the user to hold or secure the folded retainer without placing pressure on the sutures and interferring with the removal of sutures from the folded retainer. In certain embodiments of the present invention, the folder and retainer with the plurality of sutures appropriately disposed therein is hermetically sealed in an outer envelope. Preferably, the outer envelope comprises a pair of heat sealable films sealed about the periphery of the folded retainer to hermetically seal the folded retainer containing the sutures therein.

The invention will be more fully described when taken in conjunction with the accompanying drawings.

DESCRIPTION OF THE DRAWINGS

FIG. 3 is a plan view of the folder and retainer of FIG. 2 with the third cover panel folded on top of the second suture holding panel;

FIG. 4 is a plan view of the folder and retainer of FIG. 1 completely folded and locked in its final configuration;

FIG. 7 is a plan view of another embodiment of an unfolded suture folder and retainer of the present invention depicting the first loop of the sutures disposed in one configuration on the suture winding panel;

FIG. 8 is a plan view of the folder and retainer of FIG. 1 with the second suture holding panel folded on top of the suture winding panel;

FIG. 9 is a plan view of the folder and retainer of FIG. 8 with the third cover panel folded on top of the second suture holding panel; and FIG. 10 is a plan view of the completely folded and locked folder and retainer depicted in FIG. 7.

DETAILED DESCRIPTION OF THE INVENTION

Figure 1:
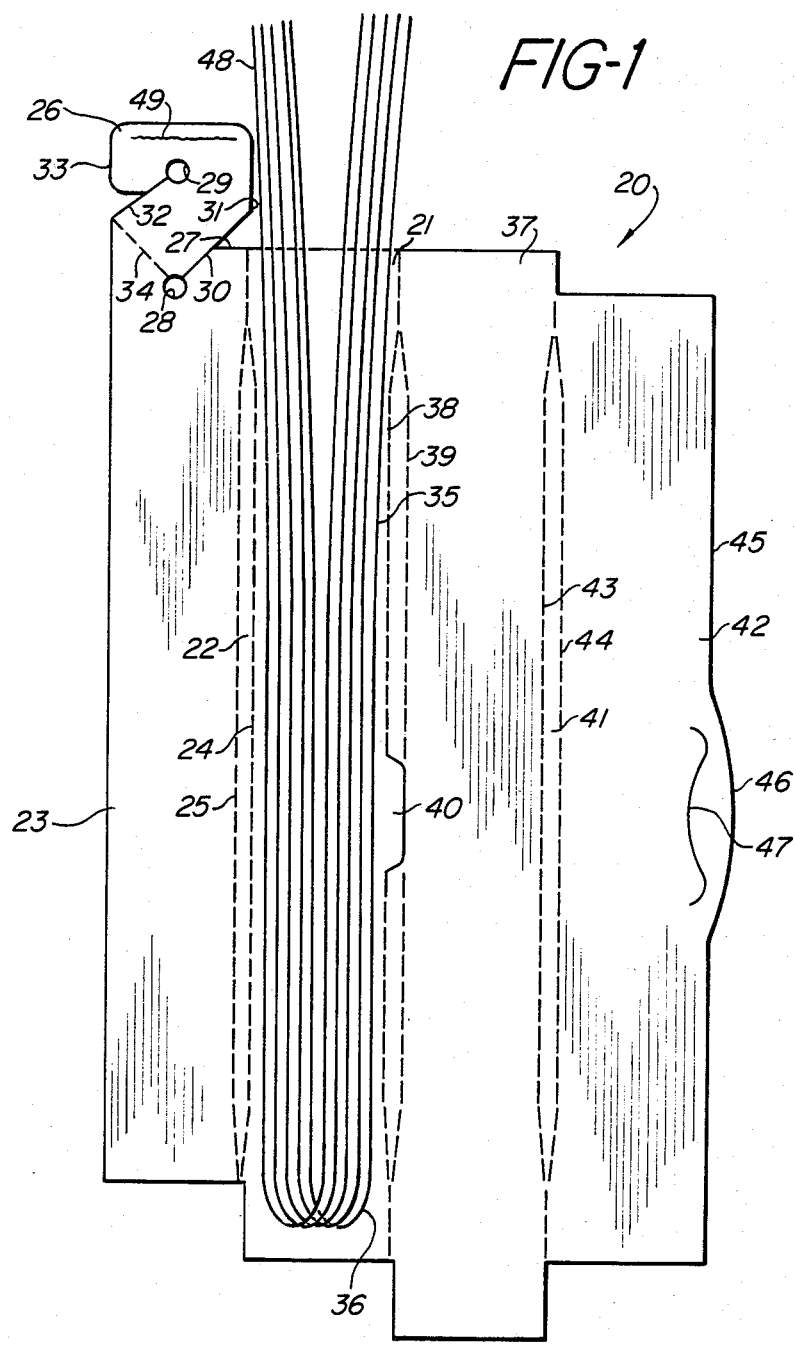
FIG. 1 is a plan view of an unfolded suture folder and retainer of the present invention depicting one disposition of the first loop of sutures on said folder.

FIGS. 1-4 illustrate the various stages in preparing and folding the folder and retainer of the present invention. In FIG. 1 there is illustrated an unfolded suture folder and retainer 20. The folder and retainer comprises a first suture winding panel 21. This panel has an elongated rectangular shape. Attached along one longitudinal edge 22 of this first suture winding panel is a second suture holding panel 23. Adjacent the line of attachment are two fold lines 24 and 25 which when folded will form a gusset between the two panels. The suture holding panel has an extension 26 connected to one of the shorter edges 27 of the panel. Disposed in the panel but immediately adjacent the extension is a first opening 28 and disposed in the extension itself is a second opening 29. In this embodiment the openings are longitudinally aligned—that is, they are disposed along the longitudinal center line of the panel. A first slit 30 extends from the first opening to an edge of the extension, and a second slit 32 extends from the edge 33 of the extension to the second opening. Also disposed from the first opening to the edge 33 of the extension is a perforated line 34. The reason for this perforated line will be explained hereinafter. The sutures 35 are laid on the suture winding panel in one single long loop 36 and there are a plurality of sutures laid on this panel. Attached to the opposite longitudinal edge of the suture winding panel is a third suture cover panel 37. Disposed along the line of adjacency between the two panels 21 and 37 are a pair of fold lines 38 and 39 which when the third suture cover panel is folded, form a gusset. Disposed in this gusset about midpoint of the panel is a slit which forms a tab 40 used to lock the folder together. Disposed on the opposite longitudinal edge 41 of this suture cover panel is a fourth suture locking panel 42. Disposed along this line of adjacency is a pair of longitudinal fold lines 43 and 44 which also for a gusset when the fourth panel is folded about the third panel. Along the outer edge 45 of this fourth locking panel is a tab 46 and disposed in the tab portion is a slit 47 used to interlock with the tab formed by the slit between the first suture winding panel and the third suture cover panel.

Figure 2:
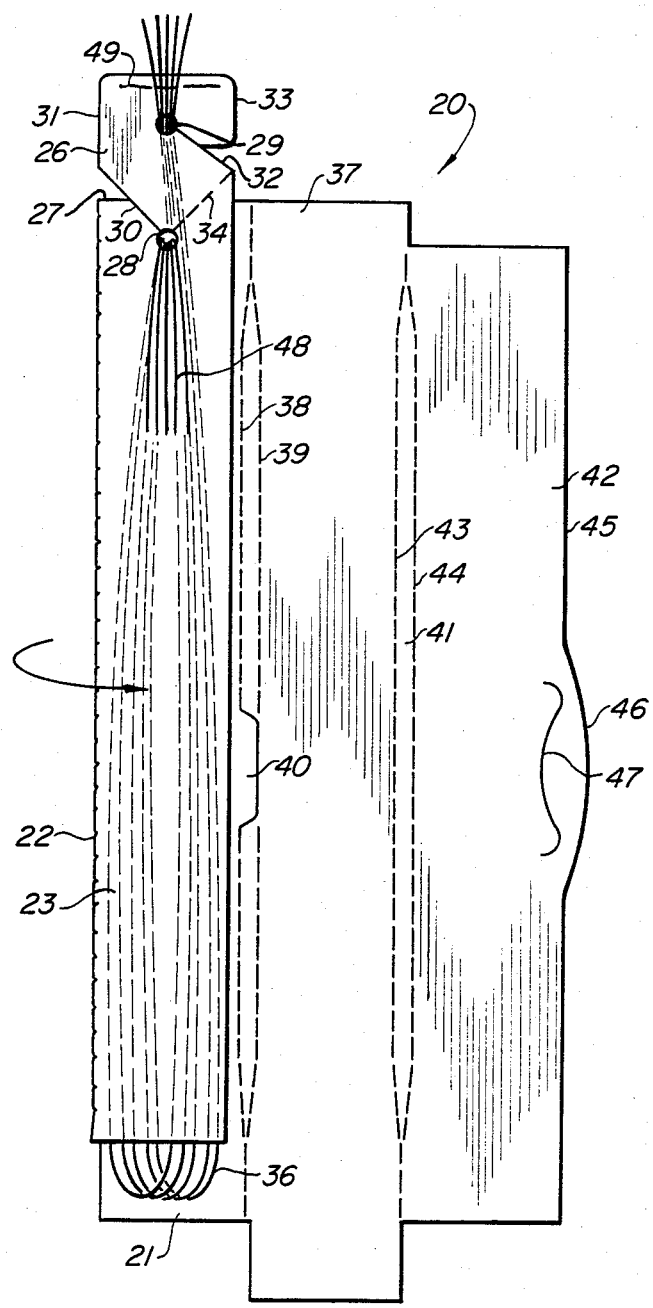
FIG. 2 is a plan view of the folder and retainer of FIG. 1 with the second suture holding panel being folded over on top of the first suture winding.

Referring to FIG. 2, the folder and retainer of FIG. 1 has had the first fold placed in it. In this illustration the suture holding panel 23 has been folded on top of the long loop 36 of sutures on the suture winding panel 21. One end of the sutures 48 has been brought through the slit 30 connecting an edge of the extension to the first opening and the other end of the sutures has been brought through the second slit 32 connecting an edge of the extension to the second opening.

As illustrated in FIG. 3, the folder and retainer of FIG. 1 has now had the second fold placed in it. In this embodiment the third suture cover panel 37 has been folded on top of the second suture holding panel 23, and as shown in FIG. 4, the folder and retainer of FIG. 1 has been completely folded and the tab 40 at the fold line between the second and third panels inserted in the slit 47 disposed in the tab 46 at the free edge of the fourth locking panel 42. In all of these figures identification means 48 is placed on the extension to identify the size and type of suture in the folder and retainer.

Figure 5:
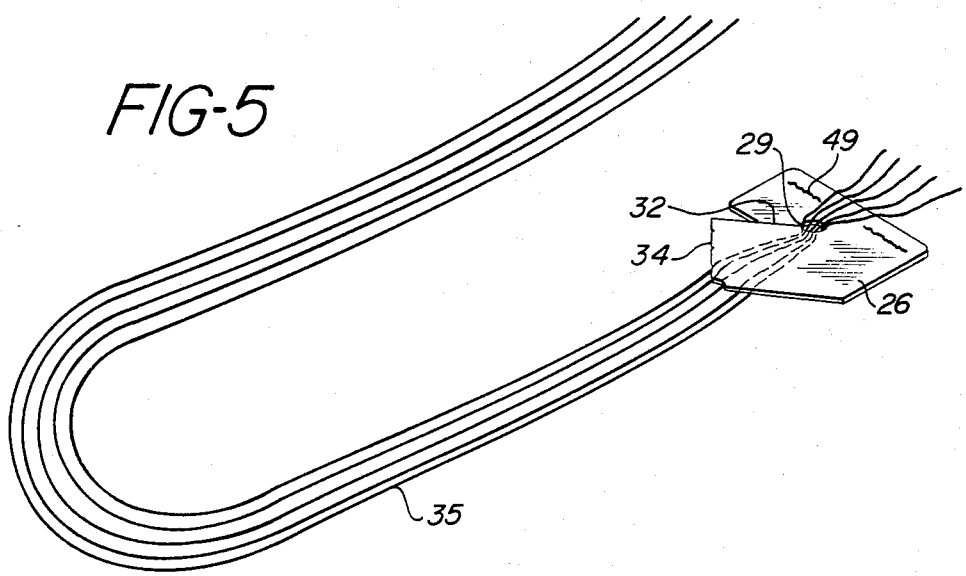
FIG. 5 is a perspective view depicting the removed extension of the folder and retainer of FIG. 1 with the sutures connected thereto.

Referring to FIG. 5, the perforated line 34 connecting the first opening to an edge of the extension has been torn to remove the extension completely from the folder and retainer. This allows all the sutures to also be removed with the extension and placed in a position to be utilized by the surgeon. The extension contains the identification of the size and style or type of sutures present. If desired, rather than removing the extension and all the sutures in the folder and retainer, an individual suture may be easily pulled from the folder and retainer in its folded condition without virtually any disruption of the other sutures in the folder and retainer.

Figure 6:
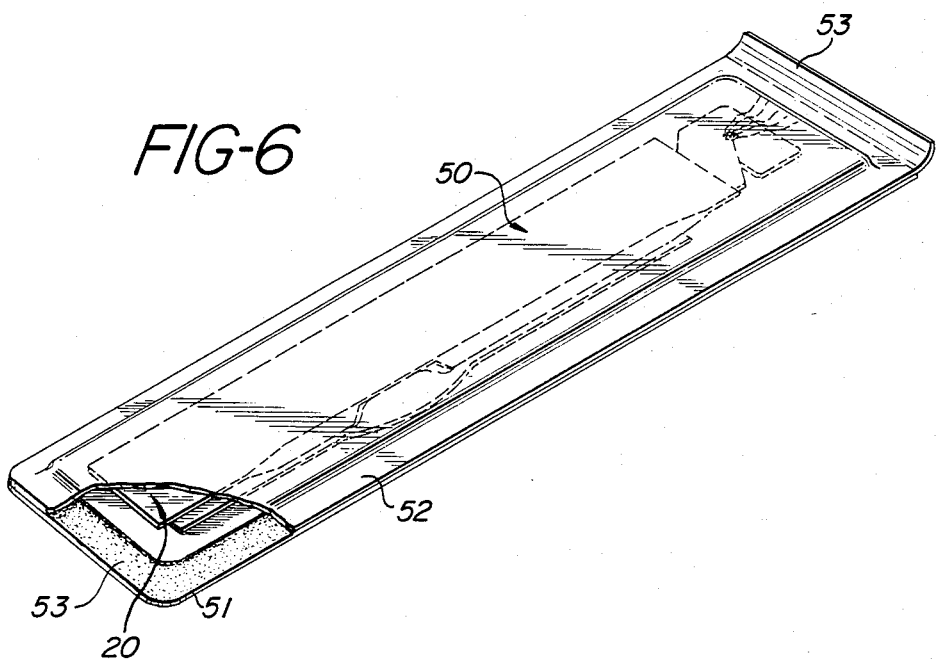
FIG. 6 is a perspective view of the folder and retainer depicted in FIG. 1 in a hermetically sealed over wrap package.

As depicted in FIG. 6 the fully folded suture folder and retainer 20 has been subsequently sealed and sterilized within a sterile outer envelope 50. The envelope is a conventional suture package envelope formed by heat sealing two panels 51 and 52 (one of a nonwoven fabric and the other of a thermoplastic film) coated on their interior surfaces with a heat sealable polymeric composition 53 together. The envelope is bonded together around the periphery of the inner folded retainer as illustrated. Other means for sealing the envelope may be used at the discretion of the practitioner. The very outer edge 54 of one of the shorter edges of the envelope may be left unsealed to allow for easy peeling away of the two outer layers to readily expose the folded suture retainer.

Suture packages illustrated in FIG. 6 are sterile and hermetically sealed and may be stored for extended periods until such time as the sutures are to be removed from the package. The outer envelope is opened to expose a sterile suture folder and retainer.

Referring to FIGS. 7-10 there is shown another embodiment of a folder and retainer 60 of the present invention. In this embodiment there is a first suture winding panel 61 which has an elongated rectangular shape. This suture winding panel has an extension 62. A first opening 63 is disposed in the suture winding panel adjacent the extension and a second opening 64 is disposed in the extension itself. The openings are slightly offset with the first opening on the longitudinal center line of the panel and the second opening slightly offset at an angle of about 15°–20° to said center line. A first slit 65 extends from an edge 66 of the extension to the first opening and a second slit 67 extends from the edge 68 of the extension to the second opening. A perforated or scored line 69 extends from the edge 68 of the extension to the first opening to allow for removal of the extension from the folder and retainer if desired. Foldably attached along one longitudinal edge of this suture winding panel is a second suture holding panel 70. A pair of fold lines 71 and 72 are disposed along this longitudinal connection so as to form a gusset when the two panels are folded together. Disposed along one shorter edge 73 of the panel 70 is a notch 74 or indentation which corresponds to the configuration of the extension as it extends into the first opening. Attached to the opposite longitudinal edge of the suture winding panel is a third suture cover panel 75. Again there are parallel fold lines 76 and 77 spaced apart to form a gusset when the third and first panels are folded about one another. Disposed in this gusset about midway between the ends of the panel is a slit 78 to form a tab 79. The third suture cover panel extends below the remaining panels to provide a tab 80 which may be held as the sutures are being removed from the folder and retainer. By placing this tab below and not in contact with any other panels, the retainer may be held without placing any pressure on the sutures or causing any hinderance to their removal. Foldably attached to the other free or longitudinal edge of the third suture cover panel is a fourth suture locking panel 81. There are a pair of parallel fold lines 82 and 83 adjacent the edges of the two panels to form a gusset when the fourth and third panels are folded together. Disposed in the free edge 84 about in the center portion of the fourth suture locking panel is a tab 85 and disposed in this tab is an appropriate slit 86.

A plurality of sutures 87 are laid in a single long loop 88 on the suture winding panel. The loop extends below the edge of the panel with the free ends 89 and 90 extending above the edge of the extension as depicted.

Referring to FIG. 8 the suture folder and retainer of FIG. 7 has had its first fold completed and the suture holding panel 70 has been folded on top of the suture winding panel. One free end 89 of the sutures has been placed through the first slit 65 connecting the edge of the extension and the first opening 63 and these ends of the sutures are laid on top of the suture holding panel. The other free end 90 of the sutures have also been brought through the first slit 65 connecting the edge of the extension to the first opening 63 and then these ends of the sutures have then been brought through the second slit 67 connecting an edge of the extension to the second opening 69.

As shown in FIG. 9 the second fold of the folder and retainer of FIG. 7 has been made. In this figure the third suture cover panel 75 has been folded on top of the suture holding panel to cover the exposed ends of the sutures. In FIG. 10 the folder and retainer of FIG. 7 has been completely folded. The fourth locking panel 81 has been folded behind the suture winding panel, the tab 79 in the fold lines between the first suture winding panel and the third suture cover panel has been inserted in the slit 86 adjacent the free edge of the fourth locking panel to lock the panels together.

The folder and retainer of the present invention provides for the packaging of a multiplicity of suture strands, and the folder and retainer allow for all the strands to be removed from the retainer at the same time or for individual strands to be removed from the container without disruption of any of the other strands in the retainer. The retainer provides for only a single loop of the sutures to be in any compartment formed between the folded panels which allows for easy removal of the sutures without disruption of the remaining sutures.

By a "single loop" it is meant a single bend of the suture. In the folder and retainer of the present invention there are as many compartments as there are single loops or bends in the suture which, of course, is determined by the length of the panels and the length of suture being packaged. It is also important that each open end of the loops be disposed at the same end of the folder and retainer. By maintaining a single loop in each compartment formed by adjacent panels and disposing all the open ends of the loops at the same end of the folder and retainer, the sutures or any individual suture may be readily removed from the folder and retainer without entangling either with itself or with adjacent sutures.

As previously mentioned, it is preferred that the two openings be aligned longitudinally. Though they may be aligned slightly offset—that is, up to 45° from the longitudinal line and preferably no greater than 30° from the line, they should not be aligned horizontally or at right angles to the longitudinal line. By correctly aligning these openings there is sufficient friction between the suture surfaces and the panels to hold the sutures in place but not sufficient friction so as to hamper the removal of a single suture from the package. The alignment of the holes in accordance with the present invention allows tension to be placed on the sutures when they are being removed from the folder and retainer. The correct hole alignment places sufficient tension on the sutures to hold them in place while allowing a pulling force to be placed on an individual suture to remove that suture while the tension maintains the remaining sutures in place in the folder and retainer to prevent entanglement of the sutures.

If the openings are aligned other than as desired, the force required to remove a suture is considerably increased and the possibility of disruption of the sutures greatly increased.

To remove sutures from the folder and retainer, light pressure may be put on the retainer. As long as the retainer has the gusset configuration, pressure is not placed on the sutures themselves and hence the light pressure on the retainer itself does not deter from removal of the sutures from the container. If desired as depicted in one embodiment, a tab on one of the panels may extend below all the other panels which tab may be gripped to allow for removal of the sutures without placing undue pressure on the sutures.

The folder and retainers of the present invention are preferably constructed of a heavy weight, relatively stiff sulfate paper board. This paper board is relatively foldable and yet sufficiently strong and stiff to support the suture and provide a rigid package. Other materials including plastic, foil, and laminates combined with each other or with paper may also be used. The retainer of the present invention may contain sutures of various sizes and lengths as desired.

The preceding description has been directed primarily to the preferred embodiments of the present invention and many variations which nevertheless employ the features thereof will be apparent to those skilled in the art. Such variations are included with the scope of the present invention.

What is claimed is:

1. An elongated rectangular suture folder and retainer for a plurality of sutures which allows for single strand dispensing of the sutures said folder and retainer comprising; a first suture winding panel having an elongated rectangular shape, a second suture holding panel having an elongated rectangular shape and foldably connected to said first panel along a longer longitudinal edge thereof, one of said first or second panels having an extension extending beyond a shorter edge of said other panel, a first opening in the panel having said extension said opening being disposed within said panel and substantially adjacent said extension, the second opening being disposed in said extension, said openings being aligned with respect to each other at an angle of 45° or less as measured from a longitudinal extending line through the panel and extension, a first slit extending from an edge of the extension to the first opening, a second slit extending from an edge of the extension to the second opening, a third cover panel foldably connected to the free longitudinal edge of said first suture winding panel and a fourth locking panel foldably connected to the free longitudinal edge of said third cover panel.

2. A suture folder and retainer according to claim 1 wherein the extension is connected to the first suture winding panel.

3. A suture folder and retainer according to claim 1 wherein the extension is connected to the second suture holding panel.

4. A suture folder and retainer according to claims 1, 2 or 3 wherein there is a slit forming a tab disposed in the folded edge between the first suture winding panel and the third suture cover panel and a tab containing a slit disposed therein said tab being disposed along the free longitudinal edge of the fourth locking panel whereby when the suture folder and retainer is fully folded, said tab in the folded edge between the first and third panels may be inserted into the slit to lock the folded retainer in its folded configuration.

5. A suture folder and retainer according to claim 1, 2, or 3 wherein there is a perforated line extending from an edge of the extension opposite the edge from which the first slit extends to the first opening.

6. A suture folder and retainer according to claim 1, 2, or 3 wherein the first opening and second opening are longitudinally aligned.

7. A suture folder and retainer according to claim 1, 2, and 3 wherein the width of the panels are substantially the same.

8. A suture folder and retainer according to claim 1, 2, or 3 wherein each of the foldable connections between the panels comprises a pair of spaced apart parallel longitudinal fold lines which form a gusset when the panels are folded.

9. A suture folder and retainer according to claim 1 containing a plurality of sutures with a single loop of said sutures being disposed between the first suture winding panel and the second suture holding panel.

10. A suture folder and retainer according to claim 9 wherein one end of the sutures is disposed through the first opening and said suture ends lay between the second suture holding panel and a third cover panel.

11. A suture folder and retainer according to claim 9 or 10 wherein an end of the sutures is disposed through the second opening in the extension.

12. A suture folder and retainer according to claim 9 or 10 wherein an end of the sutures extends through both the first opening in said panel and through second opening in said extension.

13. A suture folder and retainer according to claim 1 wherein the extension is removable from the panel to which said extension is connected.

14. A suture folder and retainer according to claim 1, 2, or 3 wherein the first opening and second opening are aligned at an angle of less than 30 degrees to each other as measured from a longitudinal line extending through the panel containing the opening.

* * * * *